(12) United States Patent
Erickson

(10) Patent No.: US 7,584,000 B2
(45) Date of Patent: *Sep. 1, 2009

(54) METHOD AND SYSTEM FOR ENERGY CONSERVATION IN IMPLANTABLE STIMULATION DEVICES

(75) Inventor: John Erickson, Plano, TX (US)

(73) Assignee: Advanced Neuromodulation Systems, Inc., Plano, TX (US)

( * ) Notice: Subject to any disclaimer, the term of this patent is extended or adjusted under 35 U.S.C. 154(b) by 280 days.

This patent is subject to a terminal disclaimer.

(21) Appl. No.: 11/383,107

(22) Filed: May 12, 2006

(65) Prior Publication Data

US 2006/0200210 A1    Sep. 7, 2006

Related U.S. Application Data

(63) Continuation of application No. 10/627,234, filed on Jul. 25, 2003, now Pat. No. 7,047,079.

(60) Provisional application No. 60/400,366, filed on Aug. 1, 2002, provisional application No. 60/398,749, filed on Jul. 26, 2002, provisional application No. 60/398,740, filed on Jul. 26, 2002, provisional application No. 60/398,704, filed on Jul. 26, 2002.

(51) Int. Cl.
*A61N 1/18* (2006.01)
(52) U.S. Cl. .......................................... 607/46; 607/16
(58) Field of Classification Search .................. 607/16, 607/29, 15, 46, 118
See application file for complete search history.

(56) References Cited

U.S. PATENT DOCUMENTS

| | | | |
|---|---|---|---|
| 3,738,371 A | 6/1973 | Raddi et al. |
| 4,326,534 A | 4/1982 | Axelgaard et al. |
| 4,390,022 A | 6/1983 | Calfee et al. |
| 4,404,972 A | 9/1983 | Gordon et al. |
| 4,503,857 A | 3/1985 | Boute et al. |
| 4,535,777 A | 8/1985 | Castel |
| 5,058,582 A | 10/1991 | Thaler |
| 5,127,402 A | 7/1992 | Mann et al. |
| 5,350,412 A | 9/1994 | Hoegnelid et al. |
| 5,350,414 A | 9/1994 | Kolen |
| 5,354,320 A | 10/1994 | Schaldach et al. |
| 5,476,483 A | 12/1995 | Bornzin et al. |
| 5,540,730 A | 7/1996 | Terry, Jr. et al. |
| 5,745,352 A | 4/1998 | Sandri et al. |
| 5,916,237 A | 6/1999 | Schu |
| 5,973,945 A | 10/1999 | Balakrishnan et al. |
| 6,099,479 A | 8/2000 | Christopherson et al. |
| 6,141,583 A | 10/2000 | Pape et al. |
| 6,185,454 B1 | 2/2001 | Thompson |
| 6,223,080 B1 | 4/2001 | Thompson |

FOREIGN PATENT DOCUMENTS

WO    8707511    12/1987

*Primary Examiner*—George R Evanisko
*Assistant Examiner*—Joseph M Dietrich
(74) *Attorney, Agent, or Firm*—Christopher S. L. Crawford; Peter Lando; Melissa Acosta

(57) ABSTRACT

The application relates to a stimulation device with power conservation functionality. In implantable devices, power supplies may be limited. Replenishing these power supplies may require costly surgery or periodic recharging depending on the model. A method may be implemented that skips or drops periodic pulses without apparently changing the frequency of the pulses. In this manner, the dropped pulses may be undetected by the patient. On the other hand, the dropped pulse represents power savings. Dropping one in ten pulses may lead to a 10% energy savings. The stimulation device may implement the method with one or more counters implemented in hardware or software.

6 Claims, 3 Drawing Sheets

METHOD AND SYSTEM FOR ENERGY CONSERVATION IN IMPLANTABLE STIMULATION DEVICES

RELATED APPLICATIONS

This application is a continuation of U.S. patent application Ser. No. 10/627,234, filed Jul. 25, 2003, now U.S. Pat. No. 7,047,079; this application also claims the benefit of (i) U.S. Provisional Patent Application Ser. No. 60/398,704, filed Jul. 26, 2002; (ii) U.S. Provisional Patent Application Ser. No. 60/398,749, filed Jul. 26, 2002; (iii) U.S. Provisional Patent Application Ser. No. 60/398,740, filed Jul. 26, 2002; and (iv) U.S. Provisional Patent Application Ser. No. 60/400,366, filed Aug. 1, 2002, all of which are incorporated herein by reference.

TECHNICAL FIELD

This invention relates to a method and apparatus for tissue stimulation. More specifically, this invention relates to a method for conserving power in implanted stimulation devices through periodic dropping of pulses.

BACKGROUND

Electronic stimulation systems may be used to control pain or motor disorders. Such systems have also been used to stimulate bone growth. For example, application of an electrical field to spinal nervous tissue can effectively mask certain types of pain transmitted from regions of the body associated with the stimulated tissue. More specifically, applying particularized electrical pulses to the spinal cord associated with regions of the body afflicted with chronic pain can induce paresthesia, or a subjective sensation of numbness or tingling, in the afflicted bodily regions. This paresthesia can effectively inhibit the transmission of non-acute pain sensations to the brain.

Electrical energy, similar to that used to inhibit pain perception, may also be used to manage the symptoms of various motor disorders, for example, tremor, dystonia, spacticity, and the like. Motor spinal nervous tissue, or nervous tissue from ventral nerve roots, transmits muscle/motor control signals. Sensory spinal nervous tissue, or nervous tissue from dorsal nerve roots, transmit pain signals.

Electrical energy may be commonly delivered through electrodes positioned external to the dural layer surrounding a spinal cord. The electrodes are carried by two primary vehicles: the percutaneous lead and the laminotomy lead.

Percutaneous leads commonly have two or more electrodes and are positioned within an epidural space through the use of an insertion, or Touhy-like, needle. An example of an eight-electrode percutaneous lead is an OCTRODE® lead manufactured by Advanced Neuromodulation Systems, Inc.

Operationally, an insertion needle is passed through the skin, between the desired vertebrae, and into an epidural space which is defined by a dural layer in combination with the surrounding vertebrae. The stimulation lead is then fed through the bore of the insertion needle and into the epidural space. Conventionally, the needle is inserted at an inferior vertebral position, for example, between vertebrae L1 and L2 (L1/L2), and the stimulation lead is advanced in a superior direction until the electrodes of the stimulation lead are positioned at a desired location within the epidural space, for example, at T10. In a lateral position, percutaneous leads are typically positioned about a physiological midline.

As an example of application, the above methodology is commonly used for the management of sympathetically maintained pain (SMP). It is generally believed that due to the sympathetic nature of SMP, stimulation leads positioned about a physiological midline provide sufficient electrical energy to interrupt the transmission of SMP signals. However, the above-described conventional technique may be used for the management of sympathetically independent pain (SIP), stimulating bone growth, and treating muscle disorders, among others.

Spinal Cord Stimulation (SCS) systems are of two types. The most common system is a totally implanted pulse generator (IPG). An IPG consists of a surgically implanted, internally-powered pulse generator and, typically, a single multi-electrode lead. The internalized power source limits the life of these systems to between one and four years. After the power source is expended, the patient is required to undergo replacement surgery to continue electrical stimulation.

The second type of SCS system is a radio frequency (RF) system. An RF system consists of a surgically implanted, passive receiver and a transmitter which is worn externally. The transmitter is connected to an antenna which is positioned externally, over the site of the implanted receiver. In operation, the transmitter communicates through an RF signal, to the implanted receiver. Just as with the IPG system, electrical stimulation is delivered via implanted leads. Differing from an IPG, however, RF systems typically possess greater power resources, thereby enabling RF systems to utilize multiple leads.

As an alternative to spinal cord stimulation, electrical energy may be delivered to selected peripheral nerves using a peripheral nerve stimulation system. Peripheral nerve stimulation involves administration of electrical energy to a localized group of peripheral nerves through placement of one or more leads at the peripheral nerve site. Unfortunately, if a patient's pain is widespread, a patient may require a plurality of stimulation leads to be implanted. The surgical procedure necessary for stimulation lead implantation is significant and can be quite painful. Additionally, because peripheral stimulation leads are implanted in "active" areas of the body (e.g., arms and legs), the leads typically lack long-term placement stability. Lead movement, or lead migration, can affect the quality of pain relief. Further, significant lead movement that undermines the intended stimulation effect may require additional corrective surgeries to reposition the stimulation leads.

In each of these cases, the stimulation device may be coupled to one or more leads with one or more electrodes. Depending on the application and the purpose of the stimulation, varying stimulation patterns and electrical fields may be desired. An applied electrical field is defined by the polarity of each electrode of the stimulation lead. Conventionally, each electrode is set as an anode (+), cathode (−), or neutral (off). For a four electrode percutaneous lead there exists approximately 50 electrode combinations. For an eight electrode percutaneous lead, the number of possible electrode combinations grows to approximately 6050. Further, various combinations of pulses and pulse frequencies may be using with sets of electrodes.

Since many typical stimulation devices are implanted in a patient, these stimulation devices have a limited power source or require periodic charging with an RF charger. In a unit having a limited power source, costly surgery is preformed to service the unit and replace the power source. In RF charged units, patients must remember to periodically charge the unit.

In a typical stimulation device, patients are encouraged to turn the units off as often as possible. Alternately, the units are cycled on and off so that the tissue is stimulated for a period of time, then not. When the stimulation is used to mask pain, turning the unit off or cycling the unit on and off may cause considerable discomfort. Further, the patient may simply ignore the request to turn the unit off.

As such, many typical stimulation devices suffer from limited power sources or periodic recharging requirements. Many other problems and disadvantages of the prior art will become apparent to one skilled in the art after comparing such prior art with the present invention as described herein.

SUMMARY

The application relates to a stimulation device with power conservation functionality. In implantable devices, power supplies may be limited. Replenishing these power supplies may require costly surgery or periodic recharging depending on the model. A method may be implemented that skips or drops periodic pulses without apparently changing the frequency of the pulses. In this manner, the dropped pulses may be undetected by the patient. On the other hand, the dropped pulse represents power savings. Dropping one in ten pulses may lead to a 10% energy savings. The stimulation device may implement the method with one or more counters implemented in hardware or software.

BRIEF DESCRIPTION OF DRAWINGS

Corresponding reference numerals indicate corresponding parts throughout the several views of the drawings.

DETAILED DESCRIPTION

Several conditions may benefit from electrical pulse stimulation or modulation of tissue. These conditions may include pain, bone growth, cardiac arrest and arrhythmias, peripheral vascular disease (PVD), angina pectoris, and various motor disorders. The electrical pulse stimulation may be delivered by a lead with several electrodes placed near the tissue to be stimulated. The lead may be connected to a stimulation device which is either implanted corporally or external to the body.

Figure 1:
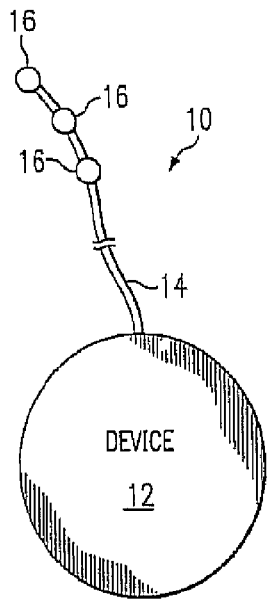
FIG. 1 is a schematic diagram depicting a stimulation device.

FIG. 1 is an exemplary implanted stimulation system 10. The device 12 may be implanted in a patient. Attached to the device 12 may be a lead 14 which may terminate in a set or array of electrodes 16. Such devices 12 may be used to treat various conditions such as arrhythmias, muscle tremors, tissue damage, and chronic pain, among others.

The device 12 may take various forms. These forms may include implantable pulse generators, neurostimulators, muscle stimulators, and defibrillators, among others. Moreover, the device may have a limited power supply.

The lead 14 and electrodes 16 may take various forms. These forms may include cylindrical leads and electrodes, paddles, and lamitrodes, among others. The lead 14 may have one or more electrodes 16 and these electrodes 16 may be shaped in accordance with various functions. Furthermore, more than one lead 14 may be attached to device 12.

The stimulation device 12 may be configured to stimulate one or more sets of electrodes with one or more pulses having various pulse characteristics. Together, the sets of electrodes and pulse characteristics make stimulation settings. For each stimulation setting, each electrode is set as an anode (+), cathode (−), or neutral (off). For a four electrode percutaneous lead there exists approximately 50 electrode combinations. For an eight electrode percutaneous lead, the number of possible electrode combinations grows to approximately 6050. These electrode settings are combined with pulse characteristics to form stimulation settings. An array of stimulation settings may be used to create a cycle. Further a set of cycles or pulses with or without variations within the cycles or among the pulses may form a repeating pattern. The repeating pattern may typically provide stimulation at frequencies between 2 and 500 HZ. However, the frequency may be more or less than this range.

If the repeating pattern includes periodically dropped or skipped pulses or cycles, energy savings may be realized without discomfort to the patient. For example, a repeating pattern of 10 cycles may have nine stimulation cycles and one dropped cycle. This pattern would result in a 10% energy saving. Alternately, the pattern may have more or less than 10 cycles. Further, the pattern may include more than one dropped cycle. In another exemplary embodiment, pulses associated with stimulation settings may be dropped within cycles.

Figure 2:
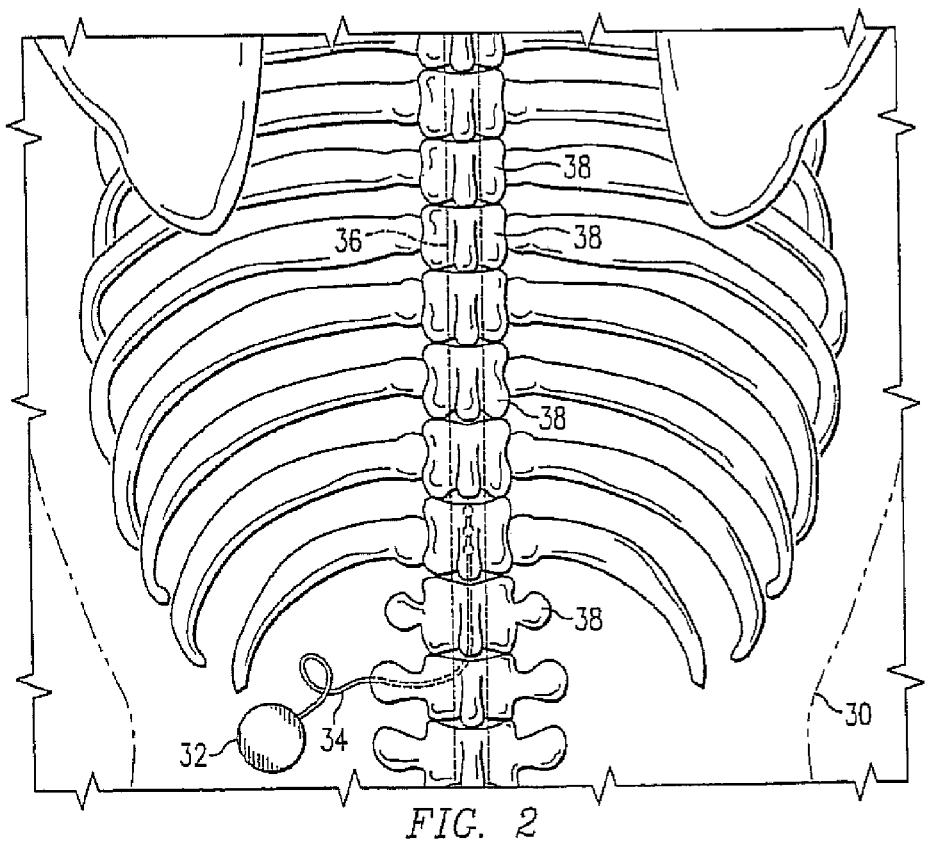
FIG. 2 is a pictorial depicting an exemplary embodiment of a implanted stimulation device.

For example the device may be act to stimulate the heart muscle, bone, spinal nervous tissue, other muscle tissue, and other nervous tissue, among others. FIG. 2 depicts an exemplary embodiment of a neurostimulator implanted in the torso 30 of an individual. In this exemplary embodiment, the device 32 may be installed such that the lead 34 extends into the spinal foramen 36 as defined by the vertebrae 38. The lead 34 may terminate in one or more electrodes. These electrodes may be used to stimulate or modulate nervous tissue. The stimulation or modulation may function to prevent muscle tremor and/or mask pain. The function and location of the effect may be affected by the location and stimulation characteristics of the electromagnetic pulses delivered by the device 32.

Figure 3:
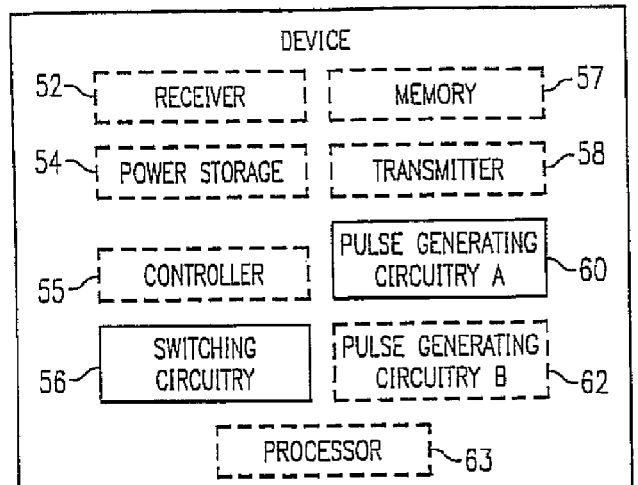
FIG. 3 is a schematic block diagram depicting an exemplary embodiment of a stimulation device.
Figure 3:
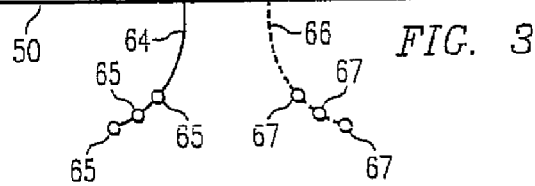

FIG. 3 is an exemplary embodiment of a stimulation device power conservation functionality. The device 50 may have a receiver 52, transmitter 58, power storage 54, controller 55, switching circuitry 56, memory 57, pulse generators 60 and 62, and processor 63, among others. Further, the device 50 may be coupled to one or more leads 64 and 66. These leads may terminate in one or more electrodes 65 and 67. However, some, all, or none of the components may be included in the device 50. Further, these components may be together, separate, or in various combinations, among others.

The receiver 52 may take various forms. These forms may include a circuitry, antenna, or coil, among others. The receiver 52 may or may not function to receive instructions and data. Further, the receiver 52 may or may not function to receive power that may be used by the device and/or stored in the power storage 54. Similarly, the transmitter 58 may take various forms including a circuitry, antenna, or coil, among others. The transmitter 58 may function to transmit data and/or instructions. However, the receiver 52 and transmitter 58 may or may not be included or may be together, separate, combine various components, among others.

The power storage 54 may take various forms. These forms may include various batteries. In an implanted device, the power is limited by the capacity of the source. Thus, power conservation may function to reduce the frequency of recharge or costly replacement.

The controller 55 may take various forms. These forms may include those discussed in FIG. 4 or other means for modulating and controlling pulses and signals. Further, aspects of the controller 55 may be implemented as software, hardware, or a combination of software and hardware.

The switching circuitry 56 may take various forms. These forms may include various contacts, relays, and switch matrices, among others. Further, the switching circuitry 56 may or may not include one or more blocking capacitors associated with connections to the leads, These blocking capacitors may block direct connection to the leads and/or function to build charge that may be discharged between signal pulses. Furthermore, the switching circuitry 56 in combination with the microprocessor 63 and/or the controller 55 may function to drop, skip, or repeat stimulation patterns.

The memory 57 may take various forms. These forms may include various forms of random access memory, read-only memory, and flash memory, among others. The memory may be accessible by the controller 55, the switching circuitry 56, and/or the processor 63. Further, the memory 57 may store various stimulation settings, repetition parameters, skipping parameters, programs, instruction sets, and other parameters, among others.

The processor 63 may take various forms. These forms may include logic circuitry or microprocessors, among others. The processor 63 may function to monitor, deliver, and control delivery of the modulation or stimulation signal. Further, the processor 63 may manipulate the switching circuitry 56. This manipulation may or may not be in conjunction with the controller 55.

The one or more pulse generators 60 and 62 may take various forms. These forms may include a clock driven circuitry, or an oscillating circuitry, among others. The pulse generator(s) 60 and 62 may deliver a electric or electromagnetic signal through the switching circuitry 56 to the leads 64 and 66 and electrodes 65 and 67. The signal may be modulated by circuitry associated with the switching circuitry 56, the controller 55, and/or the processor 63 to manipulate characteristics of the signal including amplitude, frequency, polarity, and pulse width, among others.

In one exemplary embodiment, the microprocessor 63 may interact with the switching circuitry 56 to establish electrode configurations. The pulse generator may then generate a pulse and, in combination with the microprocessor 63 and the switching circuitry 56, stimulate the tissue with a number of pulses or cycles having desired characteristics. The controller 55 may then direct the skipping or dropping of one or more pulses associated with settings in the array of settings or one or more cycles of the array. The controller may be implemented as software for use by the microprocessor or in hardware for interaction with the microprocessor and switching circuitry, among others.

Figure 4A:
FIG. 4A is a graph depicting an exemplary embodiment of a typical pulse set as delivered by the stimulation device seen in FIG. 3.
Figure 4B:
FIG. 4B is a graph depicting an exemplary embodiment of a power conserving pulse set as delivered by the stimulation device seen in FIG. 3.
Figure 4C:
FIG. 4C is a graph depicting another exemplary embodiment of a power conserving pulse set as delivered by the stimulation device seen in FIG. 3.

FIGS. 4A, 4B, and 4C are graphs depicting optional pulse patterns for a single stimulation setting. However more than one stimulation setting may be used. As such, the pattern in the graphs may also represent a pattern of pulses for an individual stimulation setting in an array of stimulation settings or cycles of an array of stimulation settings.

FIG. 4A depicts a pulse set. In this example, the pulse set has 5 pulses. FIG. 4B depicts the skipping or dropping of the fifth pulse. In this case, a 20% power conservation may be seen with limited impact on the pattern of pulses. Further, more than one pulse may be skipped in a set as seen in FIG. 4C. Similarly, dropping one pulse in ten may conserve 10% power and skipping one pulse in three may conserve 33%. The set may be larger or smaller than 10 and 3, as well. However, smaller sets may be noticeable by patients. For example if one in two pulses were skipped, the patient may perceive a change in frequency.

Figure 5:
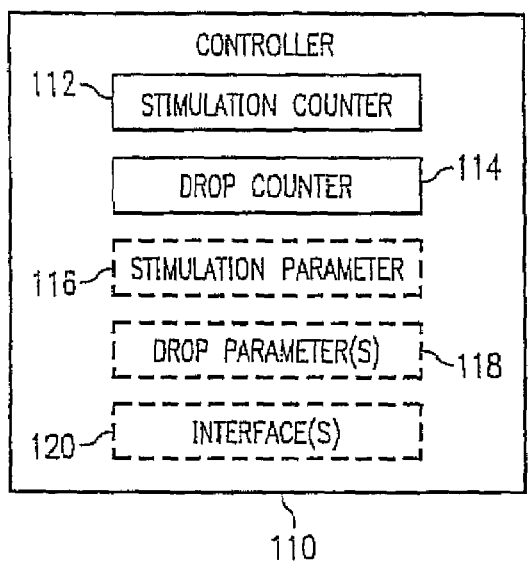
FIG. 5 is a schematic block diagram of an exemplary embodiment of a controller for use in the stimulation device seen in FIG. 3.

FIG. 5 is a schematic block diagram depicting an exemplary embodiment of a controller. Controller 110 may have one or more stimulation counters 112, one or more drop counters 114, stimulation parameters 116, drop parameters 118, and an interface 120.

In one embodiment, the one or more stimulation counters 112 counts the pulses or cycles to determine the completion of a set of stimulation pulses or cycles. In coordination, stimulation parameters 116 determines the number of stimulation pulses or cycles in a pattern. For example, a set of nine (9) stimulation pulses or cycles may be counted. However, a set of 3, 5, 20, 100 or other numbers may be counted as well.

Drop counter 114 may count dropped pulses or cycles within a set or pattern. In accordance with drop parameters 118, drop counter 114 determines the number of dropped pulses or cycles within a set or pattern. For example, counter 114 may count to one (1) dropped pulse in accordance with the drop parameter 118 before the system continues the set or pattern. Alternately, counter 114 may count to two (2) or more dropped pulses.

Together, counters 112 and 114 may be used to create patterns of stimulated and dropped pulses and/or cycles. For example, stimulation counter 112 may count nine (9) cycles. Then, the drop counter 114 may count to one (1) dropped cycle.

Both counters 112 and 114 may be reset upon completion of a pattern. Counters 112 and 114 may be implemented in hardware, software, or a combination of hardware and software. Further, the functionality of counters 112 and 114 may be combined in a single counter that uses stimulation parameter 116 and drop parameters 118. For example, skipping one pulse out of 10 may be effectively achieved by counting nine pulses and skipping the next pulse. Alternately, a more complex skipping pattern could be created using an array of parameters or a randomly generated parameter. However, various configurations may be envisaged.

Interfaces 120 may aid in communication with the microprocessor, switching circuitry, and pulse generators. When controller 110 has a hardware implementation, the interfaces may be communicative couplings between circuitries. In a software implementation, the interfaces may be software interfaces. Further, the interfaces may be combination of these.

Figure 6:
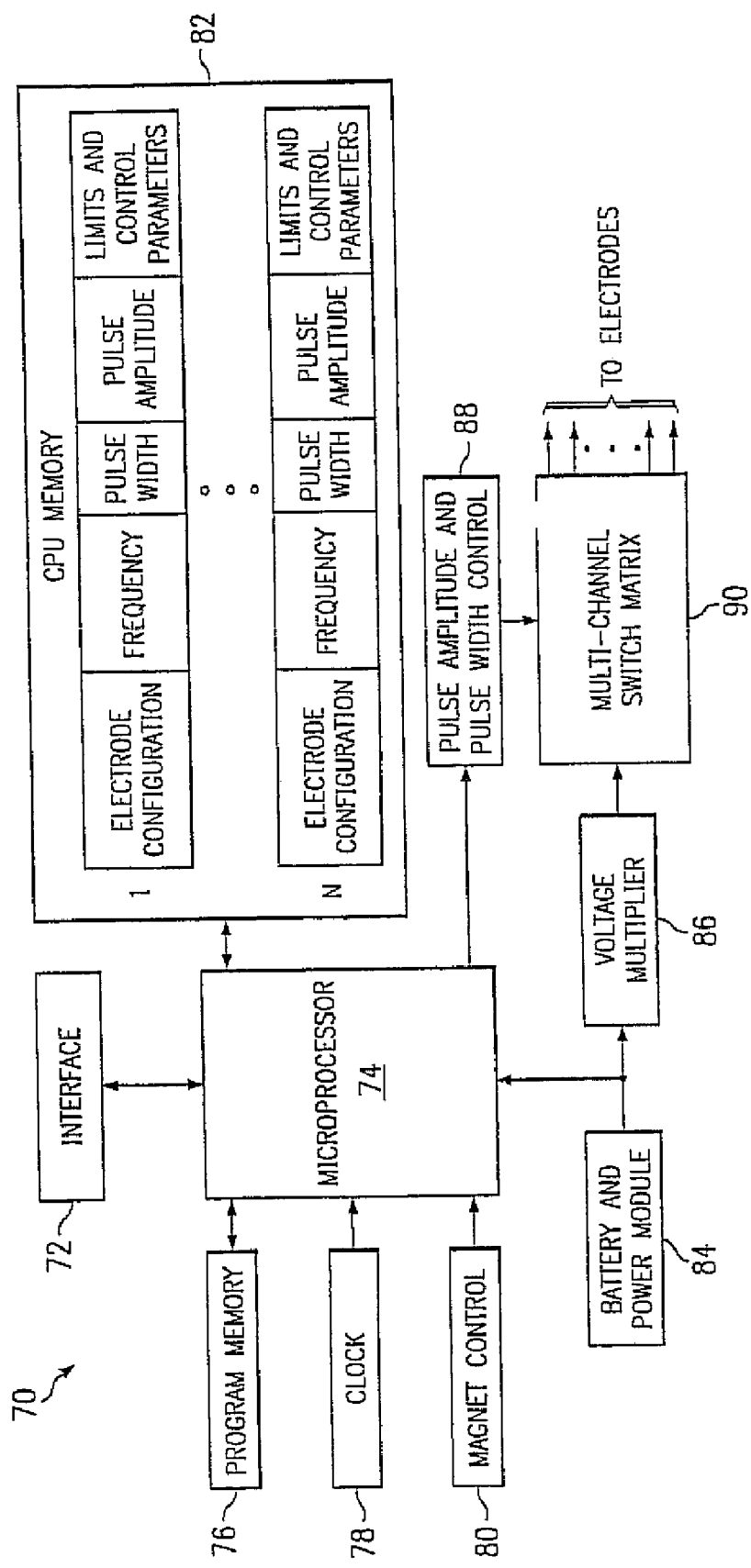
FIG. 6 is a schematic block diagram of an exemplary embodiment of the system as seen in FIG. 3.

FIG. 6 is a schematic block diagram depicting an exemplary embodiment of the system. This exemplary embodiment 70 may have a microprocessor 74, an interface 72, a program memory 76, a clock 78, a magnet control 80, a power module 84, a voltage multiplier 86, a pulse amplitude and width control 88, a CPU RAM 82, and a multi-channel switch matrix 90. However, these components may or may not be included and may be together, separate, or in various combinations.

The microprocessor 74 may take the form of various processors and logic circuitry. The microprocessor 74 may function to control pulse stimulations in accordance with settings 1 through N stored in the CPU RAM 82. Further, the microprocessor may function in accordance with programs stored in the program memory 76.

The program memory 76 may take various forms. These forms may include RAM, ROM, flash memory, and other storage mediums among others. Further, the program memory 76 may be programmed using interfaces 72.

These interfaces 72 may be accessed prior to implanting to program the microprocessor 74, program memory 76, and or CPU RAM 82. These forms may include ports or connections to handheld circuitry, computers, keyboards, displays, and program storage, among others. Alternately, the interfaces 72 may include means for interaction and programming after implanting.

A clock 78 may be coupled to the microprocessor 74. The clock may provide a signal by which the microprocessor operates and/or uses in creating stimulation pulses.

A magnet control 80 may also interface with the microprocessor. The magnet control 80 may function to turn the implantable stimulation device on or off Alternately, a receiver or other means may be used. This receiver may or may not function to provide programming instruction, charge, and on/off signals.

The system 70 may also have a power supply or battery 84. This power supply 80 may function to power the various circuitries such as the clock 78, microprocessor 74, program memory 76, and CPU RAM 82, among others. Further, the power supply 80 may be used in generating the stimulation pulses. As such, the power supply may be coupled to the microprocessor 74, a voltage multiplier, and/or a switch matrix 90.

The CPU RAM 82 may store stimulation settings 1 through N. These stimulation settings may include electrode configuration, pulse frequency, pulse width, pulse amplitude, and other limits and control parameters. The stimulation and drop parameters may or may not be stored in the CPU RAM 82 and may or may not be associated with each of the stimulation settings 1 through N. The microprocessor 74 may uses these stimulation settings and parameters in configuring the switch matrix 90, manipulating the pulse amplitude and pulse width control 88, and producing stimulation pulses.

The switch matrix 90 may or may not permit more than one lead with more than one electrode to be connected to the system 70. The switch matrix 90 may function with other components to selectively stimulate varying sets of electrodes with various pulse characteristics.

In this exemplary embodiment, the controller may be implemented in software for interpretation by the microprocessor 74. Alternately, a hardware implementation may be coupled to the microprocessor 74, pulse amplitude controller 88, and switch matrix 90. However, various embodiment of the controller system, and implementation may be envisaged.

Figure 7:
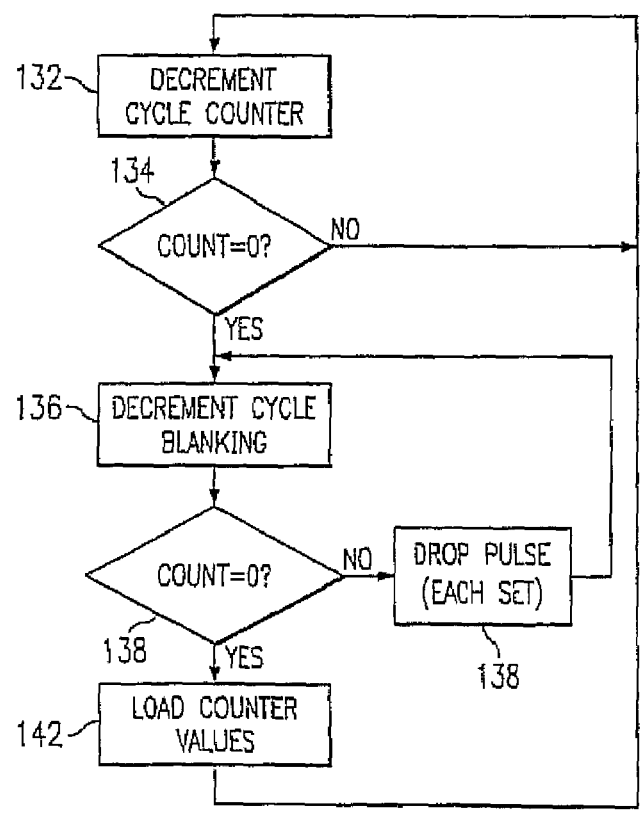
FIG. 7 is a block flow diagram of an exemplary method for use by the stimulation device as seen in FIG. 3.

FIG. 7 is a block flow diagram of an exemplary method for use by the stimulation device. In method 130, a counter is decremented with a pulse stimulation as seen in a block 132. In this case, the completion of a stimulation set would be determined if the counter reaches zero as seen in a block 134.

If the pulse marks the end of a set, a second counter may be decremented as seen in a block 136. This second counter may function to instigate and count dropped pulses as seen in a block 138 while the counter is greater than zero. Once the counter reaches zero, the set of dropped pulses or cycles is complete as seen in block 138. Both counters may then be reset or values may be loaded into the counters as seen in a block 142.

However, incrementing counters may also be used and the decision made upon reaching a predetermined number. Further, more complex patterns may be created using an array of counter values per counter or an array of counters with associated counter values.

This method may also be implemented with a single counter in which the decision as to resetting or dropping a pulse is made in accordance with parameters. The pulse may be dropped through communication with the microprocessor, switching circuitry, and/or pulse generator, among others.

As such, a stimulation device with power conservation functionality is described. In view of the above detailed description of the present invention and associated drawings, other modifications and variations will now become apparent to those skilled in the art. It should also be apparent that such other modifications and variations may be effected without departing from the spirit and scope of the present invention as set forth in the claims which follow.

The invention claimed is:

1. An implantable neurostimulator, comprising:
   means for storing a plurality of stimulation sets with each stimulation set comprising a plurality of stimulation parameters including an electrode configuration;
   means for generating a pulse and for delivering the pulse through output contacts according to stimulation parameters including an electrode configuration;
   means for controlling the means for generating by successively loading parameters from memory of the pulse generator to deliver a repeating pattern of substantially continuously occurring pulses to one or more tissues, the repeating pattern being produced by (i) cycling through the plurality of stimulation sets and (ii) loading the values of the respective stimulation sets into registers of the means for generating; wherein the means for controlling further comprises:
   (i) first means for counting each stimulation pulse in the repeating pattern of pulses to determine completion of a stimulation cycle upon counting a first number of pulses associated with a stimulation parameter;
   (ii) second means for dropping one or more pulses within the repeating pattern of pulses to form a dropped set of pulses; and
   (iii) third means for counting each of the one or more pulses in the dropped set to determine completion of the dropped set upon counting a second number of pulses associated with a drop parameter, the first means, and third means resetting upon completion of each respective stimulation cycle within the repeating pattern of pulses.

2. The implantable neurostimulator of claim 1 wherein the drop parameter is randomly generated.

3. The implantable neurostimulator of claim 1 further comprising:
   means for conducting wireless communication with a controller device, the drop parameter being controllable by the controller device.

4. The implantable neurostimulator of claim 1 wherein the means for generating a pulse and for delivering the pulse comprises a switch matrix.

5. The implantable neurostimulator of claim 1 wherein the dropped pulses are pulses corresponding to one respective stimulation set of the plurality of stimulation sets.

6. The implantable neurostimulator of claim 1 wherein the dropped pulses are pulses corresponding to each stimulation set of the plurality of stimulation sets.

\* \* \* \* \*

UNITED STATES PATENT AND TRADEMARK OFFICE
CERTIFICATE OF CORRECTION

PATENT NO. : 7,584,000 B2  Page 1 of 1
APPLICATION NO. : 11/383107
DATED : September 1, 2009
INVENTOR(S) : John Erickson It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 392 days.

Signed and Sealed this

Fourteenth Day of September, 2010

David J. Kappos
*Director of the United States Patent and Trademark Office*